(12) United States Patent
Wilden

(10) Patent No.: US 6,358,272 B1
(45) Date of Patent: Mar. 19, 2002

(54) THERAPY APPARATUS WITH LASER IRRADIATION DEVICE

(76) Inventor: Lutz Wilden, Hofäckerweg 16a, D-94051 Hauzenberg (DE)

( * ) Notice: Subject to any disclaimer, the term of this patent is extended or adjusted under 35 U.S.C. 154(b) by 0 days.

(21) Appl. No.: 09/382,821

(22) Filed: Aug. 25, 1999

Related U.S. Application Data

(62) Division of application No. 08/952,074, filed on Nov. 17, 1997, now abandoned.

(30) Foreign Application Priority Data

| May 16, 1995 | (DE) | ................................. 295 08 077 U |
| May 29, 1995 | (DE) | ................................. 295 08 844 U |
| Sep. 20, 1995 | (DE) | ................................. 295 15 096 U |
| Dec. 8, 1995 | (DE) | ................................. 295 19 482 U |
| Dec. 8, 1995 | (DE) | ................................. 295 19 481 U |
| Dec. 27, 1995 | (DE) | ................................. 295 20 581 U |

(51) Int. Cl.[7] .............................................. A61N 5/067
(52) U.S. Cl. ......................... 607/89; 606/13; 607/117
(58) Field of Search ............................. 607/89, 92, 93; 606/13, 14, 15, 17

(56) References Cited

U.S. PATENT DOCUMENTS

| 1,106,699 A | * | 8/1914 | Carroll |
| 4,224,072 A | | 9/1980 | Stewart |
| 4,570,640 A | | 2/1986 | Barsa |
| 5,030,090 A | | 7/1991 | Maeda, et al. |
| 5,280,378 A | * | 1/1994 | Lombardo .................. 359/199 |
| 5,445,146 A | | 8/1995 | Bellinger |
| 5,457,751 A | * | 10/1995 | Such .......................... 381/183 |

FOREIGN PATENT DOCUMENTS

| DE | 42 12 391 | 10/1993 |
| EP | 0 593 375 | 4/1994 |
| FR | 2 640 537 | 6/1990 |
| WO | WO 93/21992 | 11/1993 |
| WO | WO 94/28972 | 12/1994 |

* cited by examiner

*Primary Examiner*—Roy Gibson
(74) *Attorney, Agent, or Firm*—Oblon, Spivak, McClelland, Maier & Neustadt, P.C.

(57) ABSTRACT

The present invention refers, in general, to therapy apparatuses with a low-level laser irradiation device. In particular, the invention relates to an oral hygiene apparatus, an apparatus for therapy of rhinitis and acne, an apparatus for stimulation of testosterone, an inner-ear-disorder treatment apparatus for therapy of a chronic complex inner-ear disorder, an apparatus for stimulation of the central nervous system, an apparatus for therapy and prophylaxis of decubitus, as well as an apparatus for biostimulation of plants.

6 Claims, 10 Drawing Sheets

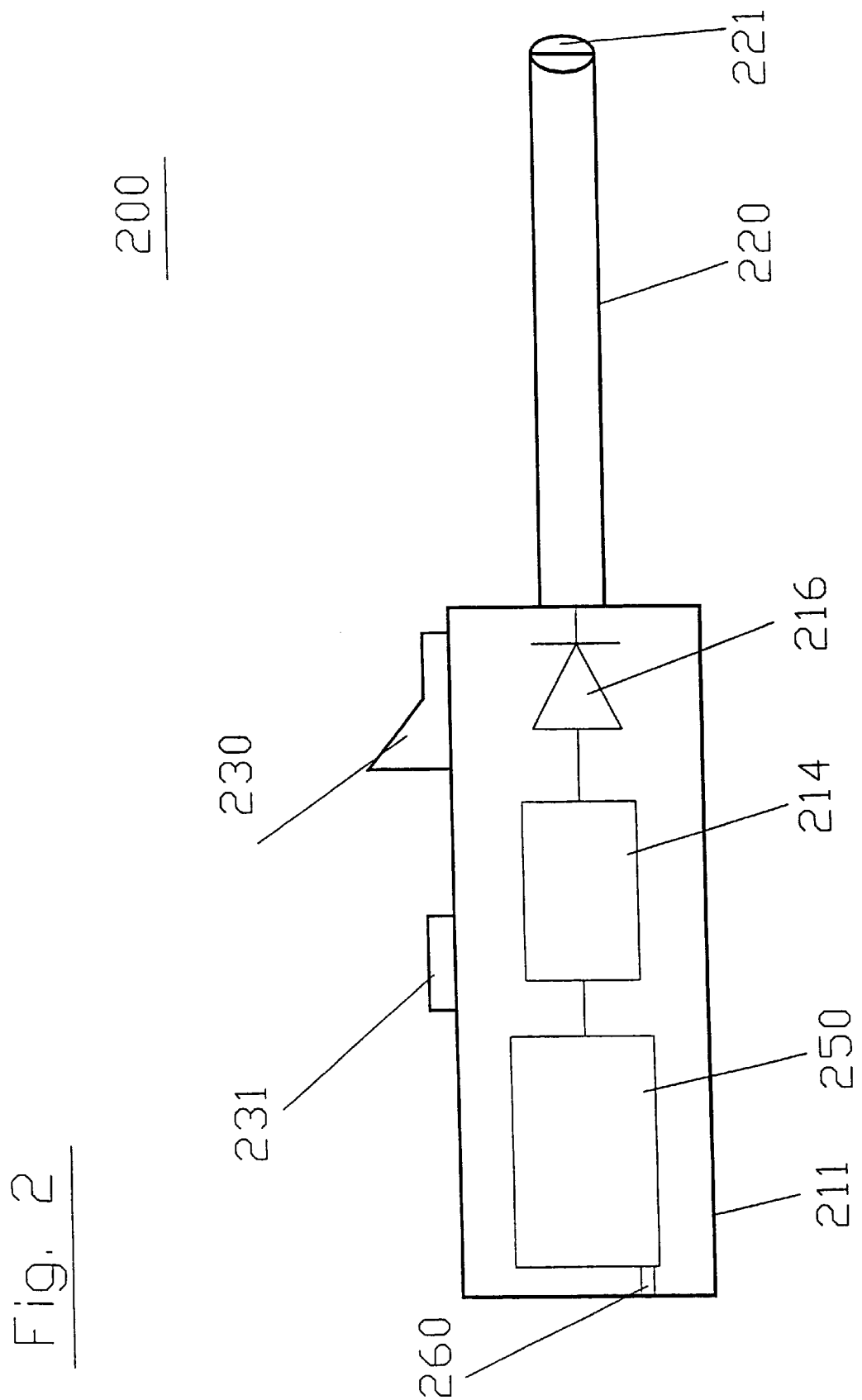

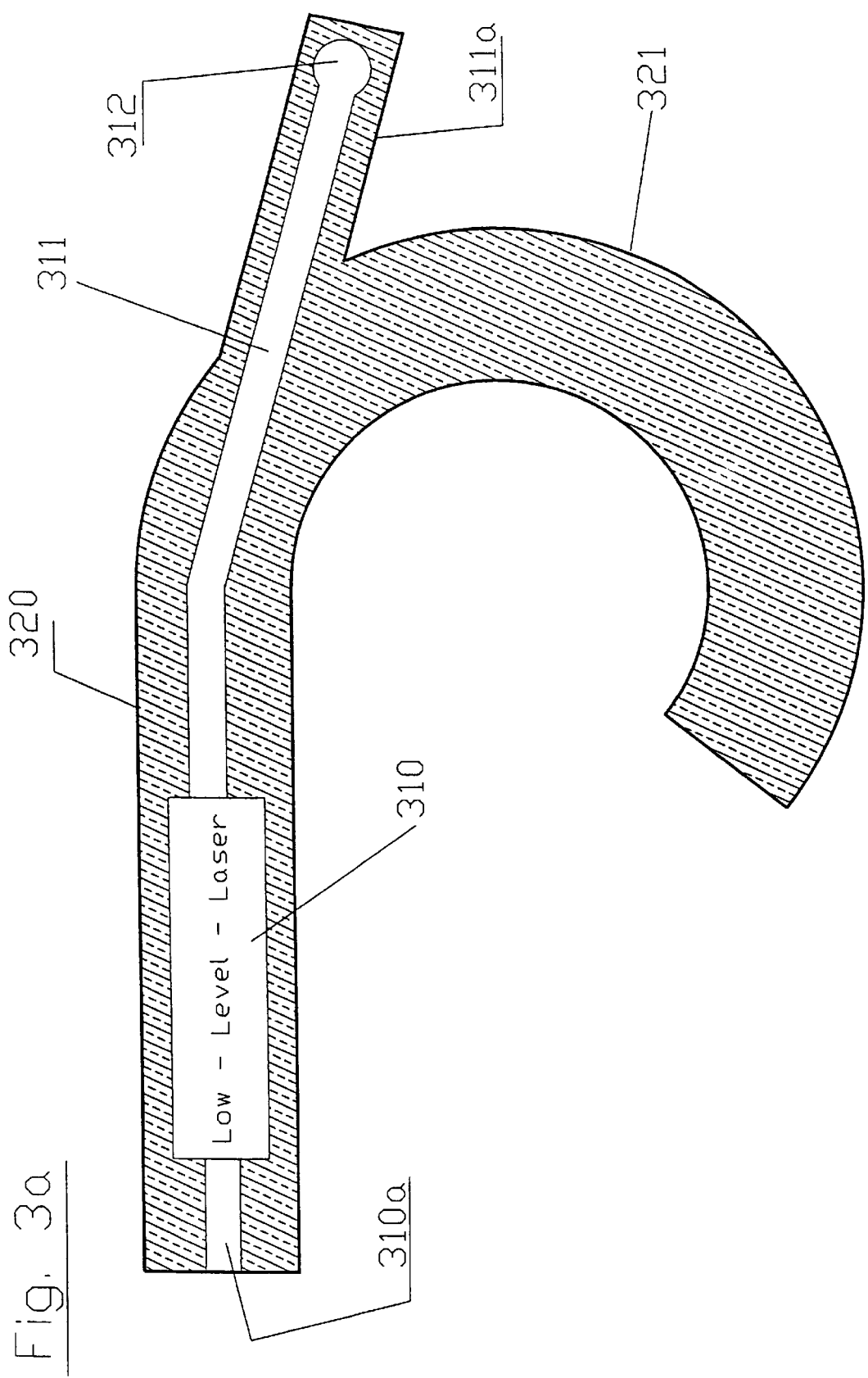

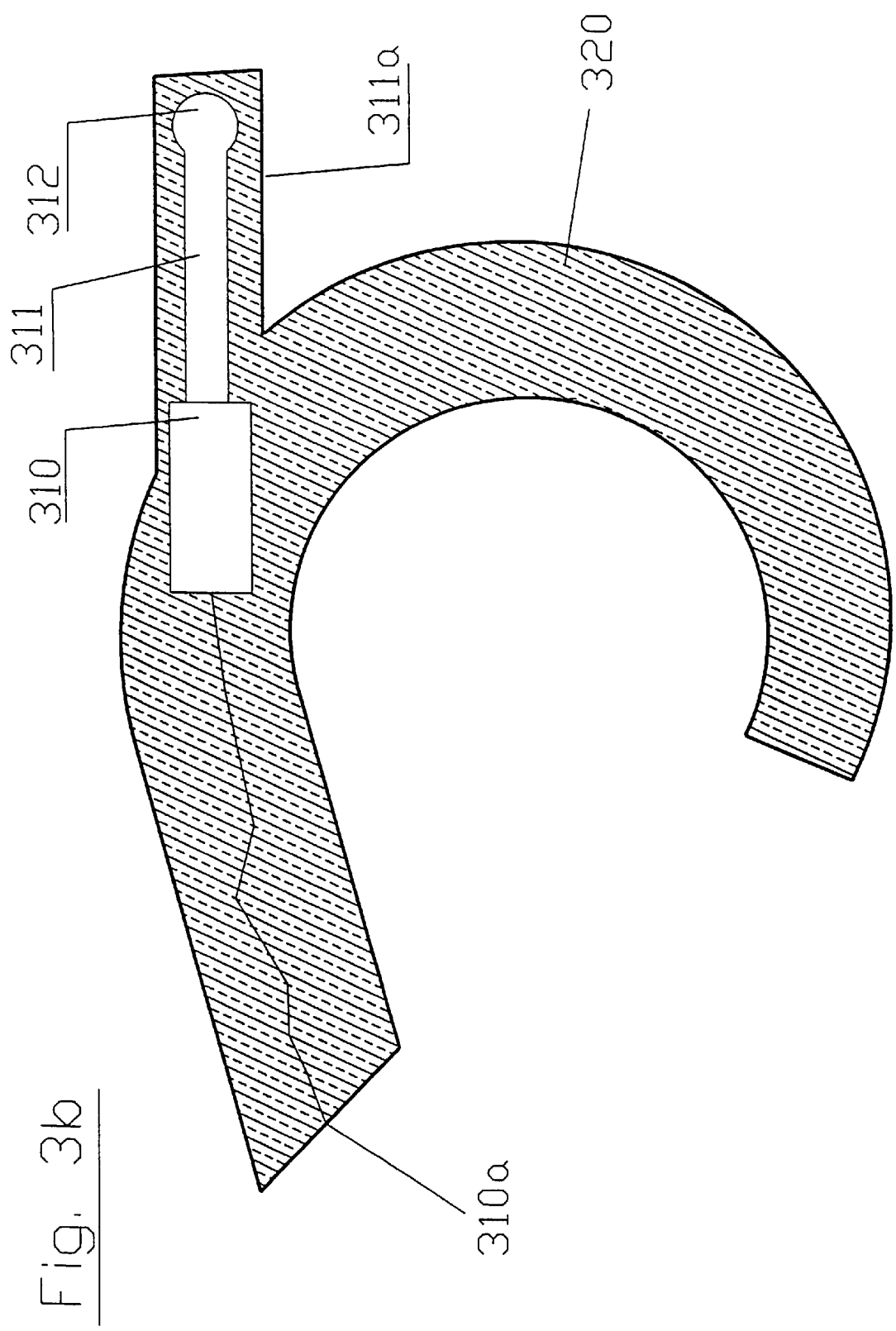

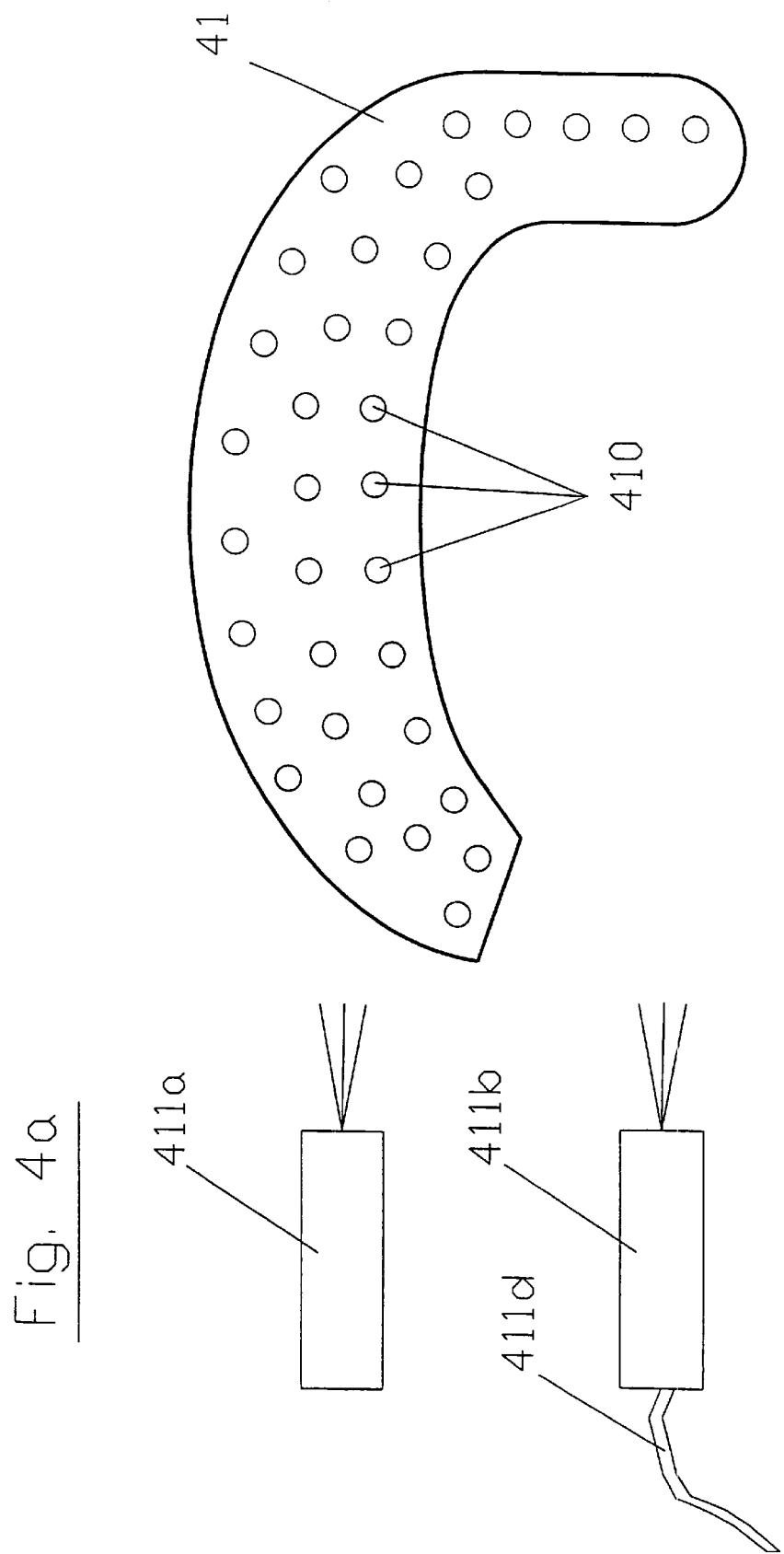

Figure 1:
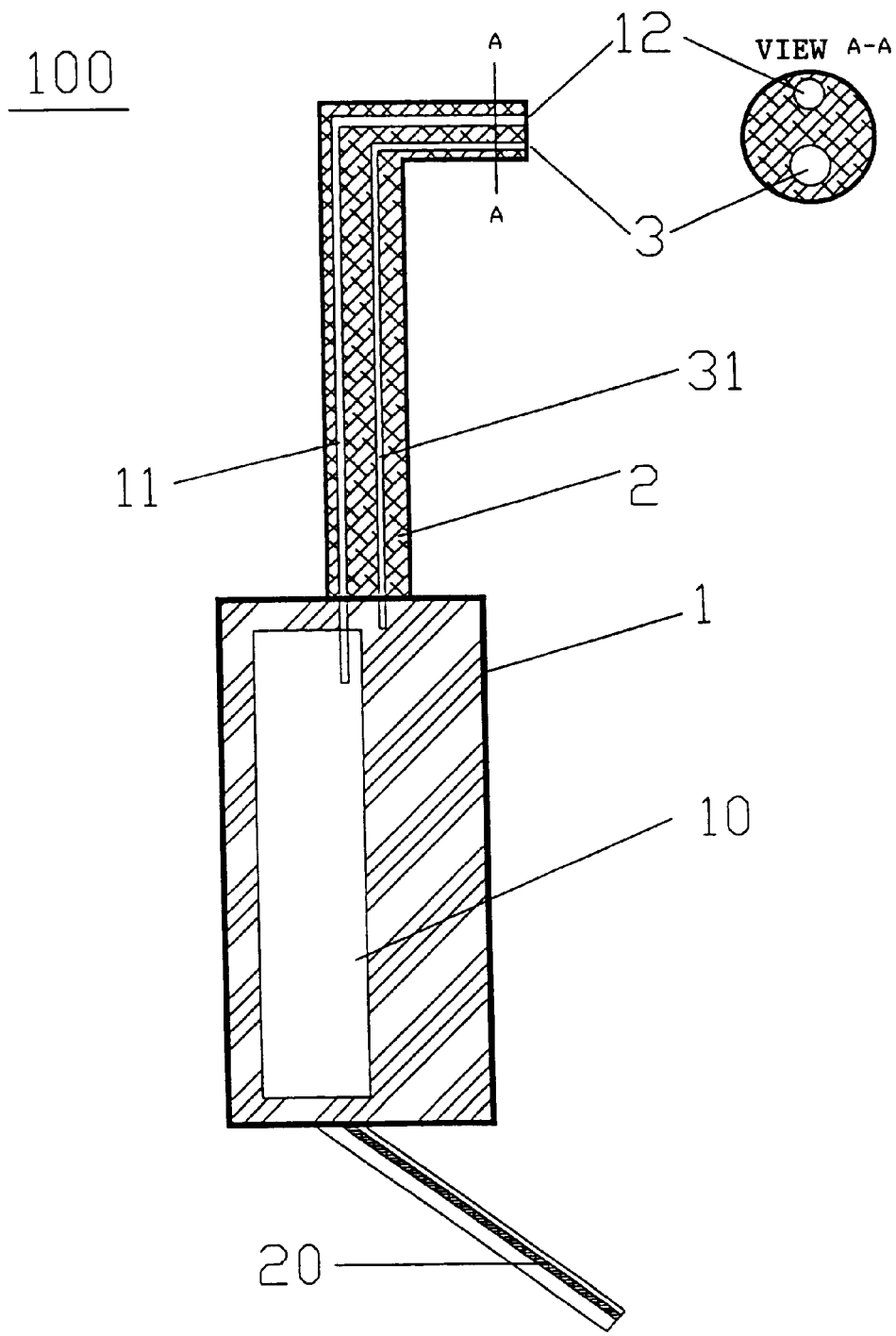

Fig. 5
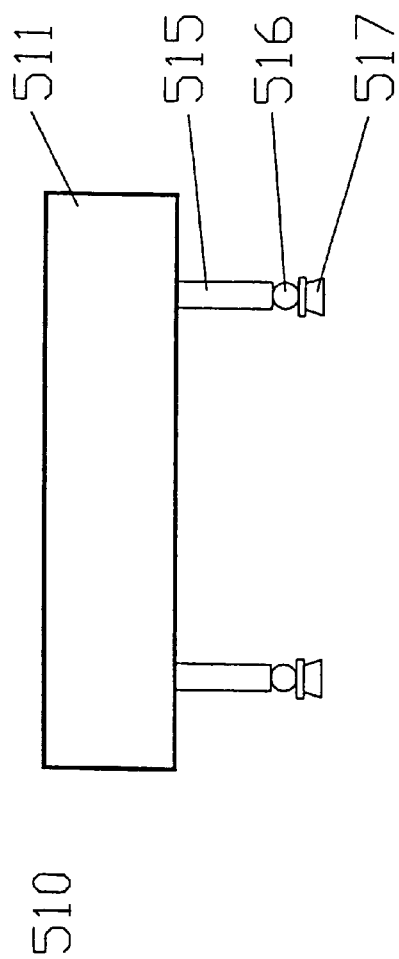
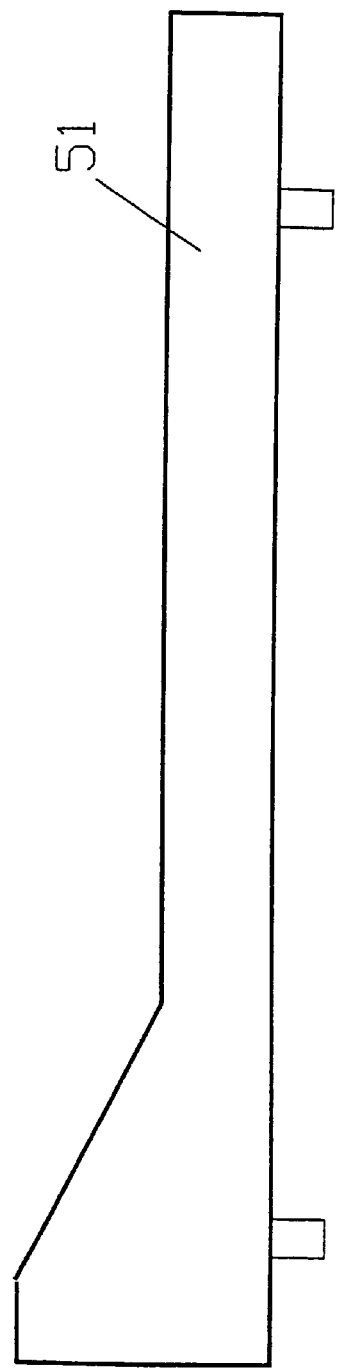

Fig. 6b
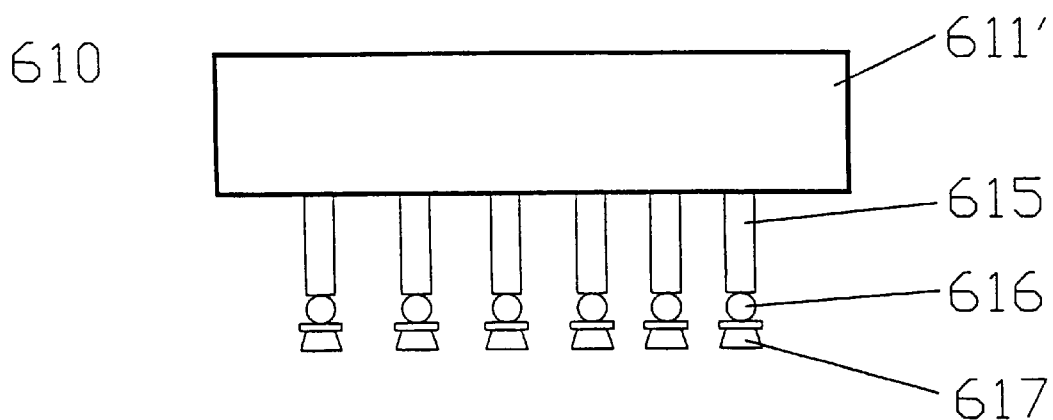
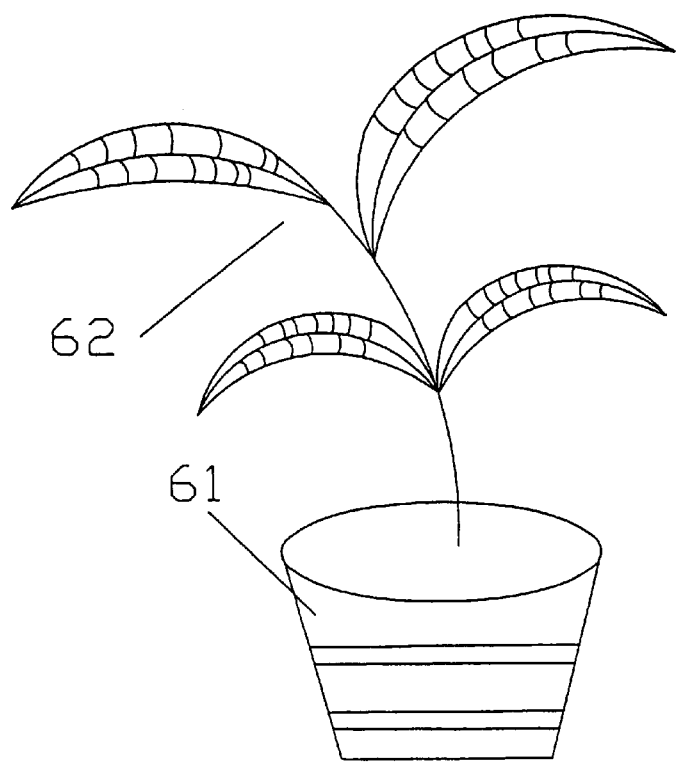

THERAPY APPARATUS WITH LASER IRRADIATION DEVICE

This application is a Div. of Ser. No. 08/952,074 filed Nov. 17, 1997, abandoned.

The present invention relates in general to therapy apparatuses with a laser irradiation device. In particular, the invention relates to an oral hygiene apparatus, an apparatus for therapy of rhinitis and acne, an apparatus for the stimulation of testosterone in the scrotum, an inner-ear-disorder treatment apparatus for therapy of a chronic complex inner-ear disorder, an apparatus for stimulating the central nervous system, an apparatus for therapy and prophylaxis of decubitus, as well as an apparatus for biostimulation of plants.

The oral hygiene apparatuses developed further by the invention are preferably such apparatuses which have a handle that is equipped with a mouthpiece which can be inserted into the mouth, with an oral hygiene device being located at its mouth-side end. Pursuant to a further development of the invention, it preferably covers such oral hygiene apparatuses that are electrically operated. Such an electrically operated oral hygiene apparatus is preferably a water pick or also an electric toothbrush. The advantages of oral hygiene apparatuses operated in such a way, with regard to keeping the teeth clean and/or massaging the gums, are sufficiently known and therefore will not be discussed further here.

In dental practices, so-called "low-level laser irradiation apparatuses" have been increasingly in use; their purpose of use is particularly the therapy and prophylaxis of periodontia, as well as the therapy and prophylaxis of stomatitis aphtosa, of herpes diseases of the lips (herpes labialis), and of the mucosa of the mouth, as well as of acne. The prefix "low-level" ("low level") for such therapeutic laser irradiation apparatuses was coined because the output, i.e. the dosage of the laser beam given off is dimensioned so that it causes no thermal effect of any kind on the body part that it impacts, in other words particularly the gums.

There are already numerous scientific publications in which the biological and therapeutic effects of coherent light with a suitable wavelength on living tissue have been studied. In many of these publications, a stimulating effect on cell metabolism has been described. A significant effect of coherent light seems to lie particularly in the fact that it stimulates mitochondrial adenosine triphosphate synthesis ("ATP synthesis"). In contrast, no cell-damaging effects of coherent light have been observed as yet, as long as its intensity, i.e. energy content is not selected at too high a level, so that the living tissue obviously cannot be damaged by such a therapeutic irradiation.

In spite of the acknowledged good therapeutic efficacy of such a low-level laser irradiation apparatus, its broader use in gum treatment has been limited by the fact that until now, such apparatuses have been available only in dental practices. Such therapy can therefore only be performed by a dentist. Since the therapeutic efficacy requires a relatively long period of treatment in many cases, the use of such low-level laser irradiation apparatuses is relatively cumbersome for most patients, so that their broader use is also limited in this regard.

The invention is based on the task of creating an oral hygiene apparatus with which therapeutic effects can be achieved.

This task is accomplished, according to the invention, with the measure indicated in the characterizing section of claim 1.

The core idea of the present invention can therefore be seen in a combination of a conventional oral hygiene apparatus and a low-level laser irradiation apparatus, where this low-level laser irradiation apparatus is arranged in the oral hygiene apparatus in such a way that the laser beam it generates can be projected into the mouth via the mouthpiece. The oral hygiene apparatus according to the invention therefore represents a combination apparatus, which not only allows conventional oral hygiene but also therapeutic treatment of the gums and the like. Such a combination apparatus can be structured both in such a way that a low-level laser irradiation apparatus according to the invention is fixed in place in a conventional oral hygiene apparatus, and in such a way that the low-level laser irradiation apparatus (for example in the form of a laser pen) is releasably attached to the oral hygiene apparatus.

In addition to the undisputed advantage that cumbersome visits to the dentist can be avoided with the combination apparatus according to the invention, this has the further advantage that the therapeutic treatment can take place significantly more often and also more regularly, so that it can be expected that the efficacy can actually be improved as compared to the laser irradiation apparatuses installed in dental practices. Because of the frequent use of the oral hygiene apparatus according to the invention, good therapeutic effects can be expected even if a low output of only 1 to 5 mW (laser class IIIA) is selected for the laser beam, for safety reasons.

The low-level laser irradiation apparatus provided according to the invention can be housed, for example, in the handle of the oral hygiene apparatus, where the laser beam it generates is passed through the mouthpiece via a light-guide device, and exits from the mouthpiece via a lens provided at its mouth-side end. Since a compact diode laser is preferably used to generate the laser beam, the total dimensions of the oral hygiene apparatus are hardly increased at all as compared with a conventional oral hygiene apparatus, particularly since the electrical energy supply can be provided via the supply that is installed in the oral hygiene apparatus for the oral hygiene device, such as a water pick or an electric toothbrush, in any case. In the case of a laser irradiation apparatus which is structured as a separate laser pen, the energy supply can be provided via a common charging station, for example in the form of a rechargeable battery stand.

The lens which projects the laser beam is preferably arranged at the mouth-side end of the mouthpiece, in such a way that the laser beam is essentially directed at the gums when the apparatus is used. Since the position of the mouthpiece when using a water pick or an electric toothbrush is essentially defined, the selection of a suitable position of the lens does not present any problems for practical situations. In order to ensure in every case that broad regions of the gums are impacted by the laser beam, it might be possible to transmit the laser beam via several lenses and/or to use a lens with a broad fan effect.

The oral hygiene apparatus according to the invention is particularly used by untrained persons, in its intended use. Improper handling of the oral hygiene apparatus can therefore particularly lead to problems if the output of the laser beam is higher than 5 mW, for example, and if the person in question aims the laser beam at particularly sensitive parts of the body, such as the eye. In order to preclude such risks, it would be possible either to limit the output to non-dangerous values right from the start, or to provide a sensor which detects whether or not the mouth-side end of the mouthpiece, i.e. the lens is located in the mouth; if the sensor detects that this is not the case, the low-level laser irradiation apparatus is automatically switched off by a corresponding control device, so that parts of the body located outside of the mouth cavity cannot be endangered in any case.

Acute or chronic as well as allergic rhinitis is one of the most frequent and also one of the more unpleasant illnesses of the nasal mucosa. If no measures for treatment are taken, cold symptoms are at least connected with a high consumption of handkerchiefs/tissues, which is both expensive and unhygienic. The treatment methods known until now, in the form of administration of medication or the like, have the disadvantage, on the other hand, that the accompanying side effects, such as excessive drying out of the mucosa, are very problematic from a medical point of view, so that the use of such medications is advised against in many cases.

In the practices of ORL physicians, apparatuses which are able to bring about relatively good healing of cold symptoms, by means of inhalation, heat treatment, etc., are already available, but a visit to the doctor is required every time for this purpose, and this is time-consuming and bothersome.

It would therefore be desirable if an easy-to-handle and nevertheless effective apparatus were available, which is able to effectively treat or actually completely heal acute or chronic rhinitis.

Another significant aspect of the present invention therefore lies in creating an apparatus for therapy and prophylaxis of acute or chronic rhinitis, which permits simple but nevertheless effective therapeutic treatment of rhinitis.

The present invention is based on the recognition that the effect of coherent light with a suitable energy and a suitable wavelength, of stimulating cell metabolism, which is already known and was explained in the introduction, could also develop a positive, i.e. regenerative and stimulating biological effect in connection with the occurrence of rhinitis. Studies by the applicant have, in fact, shown that by using coherent light, significant positive effects can be determined in the therapy and prophylaxis of rhinitis. The stated biological effects of laser light furthermore also make a positive influence on acne pustules or other small-area cosmetically disruptive inflammatory skin symptoms or scars possible. This likewise holds true for the stimulation of testosterone.

Based on this scientific recognition, the invention therefore proposes an apparatus for therapy and prophylaxis of rhinitis as well as acne, which has a low-level laser irradiation apparatus located in a one-hand housing, which apparatus generates at least one laser beam which can be directed at the interior of the nose, via a light-guide device which can be inserted into the nostril of a patient, or at acne pustules. The invention therefore creates a very simple-to-operate apparatus, which particularly can be used without the help of a doctor or therapist, can be present in every household, or even can be taken along on trips, if necessary, so that a relatively constant and therefore effective treatment can be carried out. In particular, time-consuming and expensive visits to an ORL physician or other doctors are not necessary.

As was already mentioned, the low-level laser irradiation apparatuses used by the invention are already being used in many doctors' practices for treatment of diseased tissue. Low-level laser irradiation apparatuses therefore represent a proven treatment instrument, so that the apparatus according to the invention can refer to the experience gained with such equipment, which has the result that the apparatus according to the invention can be equipped with very great reliability, in spite of extremely low cost; in particular, it is possible to keep the production and development costs within comparatively low limits.

So-called tinnitus is a chronic complex inner-ear disorder. This is a disease of the cochlea. So-called chronic vestibular vertigo, on the other hand, is a disease of the vestibular organ (the labyrinth) of the ear. Both diseases are frequent disorders of the inner ear and are preferably treated with the apparatus according to the invention; however, other diseases of the inner ear, such as inner-ear deafness, which are not being explained in greater detail here, can also be treated with this apparatus, if necessary.

For the person affected, tinnitus expresses itself as a permanent whistling or uninterrupted buzzing in certain frequencies. This permanent whistling is extremely unpleasant for the person affected, for one thing, and can even result in psychological problems, while on the other hand the ability to hear. in the related frequency range is restricted accordingly. For this reason, greater efforts have recently been made to find suitable therapies for tinnitus.

Recently, the use of a low-level laser has also proven to be one of the most successful therapies for treatment of tinnitus. In the case of tinnitus treatment by means of such a low-level laser, significant healing effects were achieved, particularly by means of irradiation via the mastoid (at a location approximately 2 cm behind the earlobe, or via the auditory canal. Vertigo and inner-ear deafness were also successfully treated with this method.

The stated low-level laser devices are special apparatuses which are currently available only in doctors' practices and clinics that have been equipped with them. The patient affected must therefore visit such a practice or clinic for every treatment of an inner-ear disorder or tinnitus. Since a noticeable healing effect of low-level laser irradiation generally occurs only after a relatively long period of time, the patient must visit the practice or clinic frequently. This is a bother for the patient, on the one hand, and on the other hand has the disadvantage that correspondingly high treatment costs occur.

Another significant aspect of the present invention therefore lies in the fact of creating an inner-ear-disorder treatment apparatus with which treatment costs can be clearly reduced.

The invention proposes, in this connection, that a low-level laser irradiation device be provided, which can be removably attached to the ear of a patient, by means of a suitable attachment device, in such a way that the laser beam acts on at least a predetermined region of the ear. The core idea behind this measure can therefore be viewed as creating a low-level laser irradiation device which the patient constantly carries with him/her for the duration of treatment, so that correspondingly intensive treatment takes place, which leads to the expectation that the prospects of healing achieved with the apparatus according to the invention will be even higher than the ones achieved with the low-level laser devices available in doctors, practices and clinics. Another advantage of the inner-ear-disorder treatment apparatus lies in the fact that in principle, it is sufficient if the apparatus is fitted by a therapist at the beginning of treatment; no additional visits to the doctor are necessary for the patient, so that therapy is easier for the patient. The treatment costs connected with the visits to the doctor or clinic are also eliminated, so that overall, great cost advantages can be achieved.

The low-level laser irradiation device of the inner-ear-disorder treatment apparatus according to the invention can be housed in the attachment device itself, where in this case preferably a light-guide device is provided, via which the laser beam generated by the laser irradiation device is passed to a lens, if necessary, from which the laser beam exits and acts on the predetermined region(s). The light guide preferably comprises a material which permits the therapist fitting the apparatus to adjust the position of the light exit, i.e. the predetermined region of effect, by bending or swiveling it, or the like. If necessary, an adjustment device can also be provided between the attachment device and the light-guide device, making it possible to change the length and/or direction of the light-guide device by means of screw connections or the like.

As an alternative, the low-level laser irradiation device of the inner-ear-disorder treatment apparatus according to the invention can also be a separate unit, the laser beam of which is passed to a lens, possibly located at the end of a flexible light-guide device, where in this case only the lens and/or the end of the light-guide device is attached to the ear by means of the attachment device. In this variant of the invention, the laser irradiation device is placed in the patient's shirt pocket or pants pocket, or attached to the patient's belt. This variant of the invention is particularly used if the low-level laser irradiation device and/or its battery power supply is relatively large and/or heavy.

Another significant aspect of this device lies in the fact that a device already present is used as the attachment device. Such a device can be, for example, a glasses frame, a hearing aid, a tinnitus masker, or a combination apparatus consisting of a tinnitus masker and a hearing aid (a tinnitus masker is a small loudspeaker which generates a noise in the frequency of the tinnitus, so that the patient has the impression that the tinnitus is an external noise). Of course it is also possible to provide a separate attachment device for the inner-ear-disorder treatment apparatus, such as an earpiece which can be attached to the ear, a part which can be inserted into the ear (comparable to an inner-ear hearing aid), or a metal strap which can be placed on the head, comparable to a set of headphones.

Disorders of the central nervous system of a human being are known to occur in more or less serious form. In this connection, Alzheimer's disease, which is well known, can be particularly mentioned. Many people are furthermore affected by a general or specific brain performance weakness, suffer from depressions, concentration disorders, etc. It would therefore be desirable to have an easy-to-handle and nevertheless effective apparatus available which effectively treats or actually completely eliminates the diseases mentioned above, by means of suitable stimulation of the central nervous system. Such an apparatus could also be used for a general increase in cerebral performance, if applicable.

Another significant aspect of the present invention therefore lies in creating an apparatus for stimulating the central nervous system, which permits simple and nevertheless effective therapeutic treatment of cerebral diseases.

The present aspect of the invention is based on the recognition that the known effect of coherent light with a suitable energy and a suitable wavelength, that of stimulating cell metabolism, could also develop a positive, i.e. regenerative and stimulating biological effect in the central nervous system. Studies by the applicant have, in fact, shown that by using coherent light, significant positive effects on the central nervous system can be determined. It can therefore be expected that the use of coherent light to stimulate the central nervous system, as proposed by the invention, is suitable for treating or actually completely eliminating the diseases stated above, particularly Alzheimer's disease, general or specific brain performance weakness, depressions, concentration disorders, etc., with therapeutic efficacy.

Based on this scientific recognition, the invention therefore proposes an apparatus for stimulating the central nervous system, which has a low-level laser irradiation device which generates at least one laser beam, which acts on at least one predetermined region of the patient's skin, preferably in the immediate vicinity of the central nervous system to be stimulated. Because such low-level laser irradiation devices are already numerously in use (see explanations above), these represent a proven treatment system, so that the apparatus according to the invention can refer to the experience gained with such equipment, which has the result that the apparatus according to the invention can be equipped with very great reliability, in spite of extremely low cost; it is also possible to keep the production and development costs within comparatively low limits.

Another aspect lies in the fact that the central nervous system stimulation device is able to treat various regions of the central nervous system from the outside, either simultaneously, or, depending on the indications, partially with the laser beam or the laser beams of the low-level laser irradiation device. This can be done, for example, in that the low-level laser irradiation device acts on the patient's head. For this purpose, it is particularly advantageous if a helmet-like or hood-like cap for the patient's head is provided, where this cap preferably bears a plurality of laser beam transmission elements, the laser beams of which are directed into the interior of the cap. This makes it possible to treat the central nervous system relatively from the outside; nevertheless, targeted treatment by regions can take place in very simple manner, in that the corresponding transmission elements are selectively activated.

The cap can be attached, for example, on a pivoting holder, so that it can be easily placed over the patient's head like the hood of a hair dryer, and in this way, the distance between the transmission elements and the patient's scalp can also be adjusted in extremely simple manner. To adjust a defined distance from the scalp, spacers can be provided inside the cap, as an alternative to or additionally to this measure, which keep the inside wall of the cap and therefore the laser beam transmission elements at a predetermined distance from the patient's scalp. Such spacers are particularly useful if the cap according to the invention is set on without a holder, i.e. represents a type of helmet.

The laser beam transmission elements can each be formed, for example, of a laser diode, each of which is supplied with power from its own battery or from a central power supply. As an alternative to this, each laser beam transmission element can comprise a light-guide device with a lens at its end, if necessary. At the other end, all the laser beam transmission elements are supplied from a common laser light source, for example. As an alternative to this, a separate laser light source can be provided for each or for at least part of the laser beam transmission elements, so that the, possibility of operating all the laser beam transmission elements with a different frequency and/or output exists. The laser light sources can either be part of the hood or be arranged in an external apparatus.

Although the stated helmet-like or hood-like cap represents the preferred method of therapeutic treatment of a patient's head, the low-level laser irradiation device can also act on the regions of the central nervous system to be impacted in any different way. For example, it is possible to affix the low-level laser irradiation device on pivot arms, sensors, external beam emitters, or the like. If necessary, it is even possible to structure the low-level laser irradiation device as part of a whole-body treatment apparatus, in the nature of a tanning bed. In every case, however, measures should be taken which reliably prevent the intensity of the laser beams given off from being only so high that sensitivity body parts, such as particularly the eye, are not damaged by it.

The apparatus for stimulating the central nervous system created by the invention can be designed both as a therapeutic (medical/technical) apparatus and as an apparatus which can be used by untrained persons under their own responsibility. Furthermore, it is possible to structure such an apparatus as a coin-operated apparatus, which operates for a predetermined period of time when the correct amount in coins is inserted.

It is generally known that in cases of extended bed rest (such as in an old-age home, after an extended hospital stay, or during out-patient care), the problem of bed sores arises; this phenomenon, referred to in technical circles as decubitus, represents a serious illness of the body regions affected, and therefore requires careful treatment. Nevertheless, it has proven to be difficult until now to treat decubitus in suitable manner; prevention or prophylaxis was also hardly possible until now.

It would therefore be desirable to have available an easy-to-handle but nevertheless effective apparatus which can prevent the occurrence of decubitus by suitable stimulation, or can effectively treat or even completely eliminate it after it has occurred.

Another significant aspect of the present invention therefore lies in creating an apparatus for therapy and prophylaxis of decubitus, which permits simple but nevertheless effective therapeutic treatment of decubitus.

The present invention again utilizes the recognition that the effect of coherent light with a suitable energy and a suitable wavelength, of stimulating cell metabolism, which is actually known, could also develop a positive, i.e. regenerative and stimulating biological effect when decubitus occurs, if necessary. Studies by the applicant have, in fact, shown that by using coherent light, significant positive effects can be found in the therapy and prophylaxis of decubitus.

Based on this scientific recognition, the invention therefore proposes an apparatus for the therapy and prophylaxis of decubitus, which has a low-level laser irradiation device which generates at least one laser beam which acts on specific region of a patient's skin.

The apparatus according to the invention can be used to particular advantage if a plurality of laser beam transmission elements is provided, which can be accordingly aimed at different regions of the patient's skin, so that uniform treatment of the entire affected skin area is possible. Furthermore, it is advantageous to provide a timer which deactivates the laser beam transmission elements after expiration of a preselected time span. In this manner, every patient can be subjected to a predetermined treatment period of 30 minutes, for example, without nursing personnel having to be present.

In order to achieve a uniform impact of the laser beams on the skin areas to be subjected to the decubitus therapy, it is possible to use a scatter lens to spread the laser beam out. As an alternative to or additionally to this, it would be possible to cyclically change the exit angle of the laser beam transmission elements by means of a motor, in such a way that the sore area of the patient's skin is impacted by the laser beams in a cyclic sequence.

This apparatus can particularly be used for home treatment (including self-treatment by the patient) of chronic skin diseases (skin therapy) as well as for thymus stimulation.

Both for decorative plants used in homes, and for commercial raising of plants, it is the supreme goal to promote the growth of the plants in question as much as possible. Furthermore, the plants' resistance to disease or pests is to be increased. As a rule, these goals are achieved by chemical fertilizers and/or chemical pesticides. The disadvantages of administering such chemical agents are sufficiently known and therefore require no further explanation. In order to prevent or at least reduce the use of such chemical agents, it has therefore already been considered to promote plant growth in an alternative manner, for example by means of biological stimulation. However, no apparatuses which make reliable biological stimulation of plants possible have become known until now.

Another significant aspect of the present invention therefore lies in creating an apparatus for biostimulation of plants, which permits simple but nevertheless effective biostimulation of plants.

According to the invention, it was recognized for the first time that the effect of coherent light with a suitable energy and a suitable wavelength, of stimulating cell metabolism, can also develop a positive, i.e. regenerative and stimulating biological effect in the cell system of plants. Studies by the applicant have, in fact, shown that by using coherent light, significant positive effects on the cell system of plants can be found. It can therefore be expected that the use of coherent light for biostimulation of plants, as proposed by the invention, is suitable for strongly stimulating the growth of the plants in question, and also increasing the plants' resistance to diseases or pests.

Based on this scientific recognition, the invention therefore proposed an apparatus for the biostimulation of plants, which has a low-level laser irradiation device which generates at least one laser beam which acts on specific regions of the plants' surface. The apparatus according to the invention can be effectively used both for decorative plants or the like, and for commercial purposes, such as in greenhouses. In any case, significant amounts of chemical agents can be saved, while nevertheless good growth stimulation and high resistance to diseases can be achieved.

The apparatus according to the invention can be used to particular advantage if a plurality of laser beam transmission elements is provided, which can be accordingly directed at various regions of the plant(s) to be stimulated, so that uniform treatment of the entire surface of the plant(s) is possible. Furthermore, it is advantageous to provide a manually operated or automatically functioning control device, which activates one or more laser beam transmission elements with a suitable wavelength in each instance, or changes its/their output. This makes optimum adaptation of the apparatus according to the invention to the plant's/plants' growth possible.

Studies have shown that great success can be achieved with the apparatuses according to the invention particularly if the low-level laser irradiation device generates a laser beam with a wavelength which extends from the ultraviolet range to the near infrared range, in other words from approximately 180 nm to approximately 1000 nm, where the output of the apparatuses intended for self-treatment should preferably lie between 1 mW and 120 mW, especially between 1 mW and 5 mW; the apparatus therefore corresponds to the laser specification Class IIIB and IIIA, respectively. If, on the other hand, the apparatuses are intended for professional use-by trained personnel, low-level laser irradiation devices with an output of max. 500 mW are used.

If necessary, it can be considered to provide the apparatus with a manual adjustment device, by means of which the output of the low-level laser irradiation device and/or the wavelength of the laser beam can be adjusted to a value that can be selected by the patient. The low-level laser irradiation device can either operate continuously or also in pulsing operation, where the desired method of operation can be adjusted with a corresponding selector switch, if applicable.

Figure 3C:
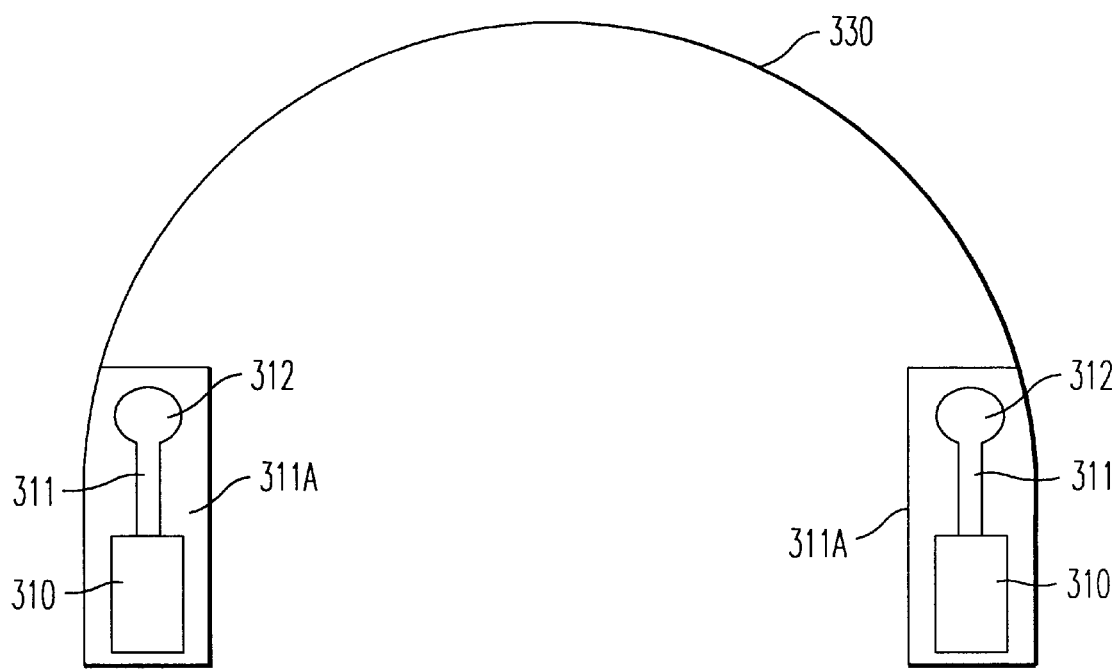

The invention will be explained in greater detail below, on the basis of a description of exemplary embodiments, and referring to the drawing. This shows:

FIG. 1 an embodiment of the oral hygiene apparatus;

FIG. 2 an embodiment of the apparatus (200) for therapy of rhinitis and acne, which can also be used for stimulation of testosterone in the scrotum;

FIGS. 3A to 3C three embodiments of an inner-ear-disorder treatment apparatus for therapy of a chronic complex inner-ear disorder.

Figure 4B:
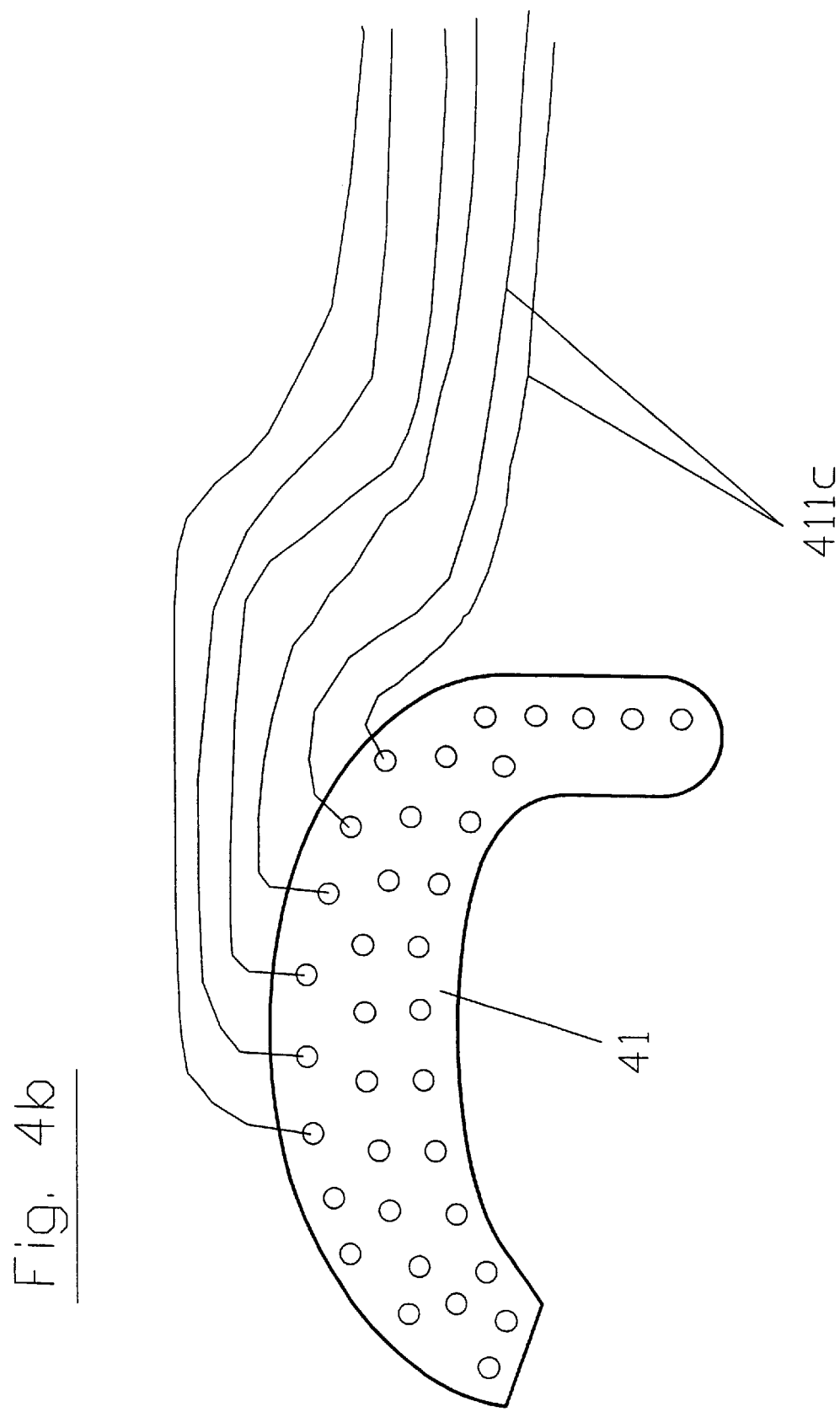
Figure 6A:
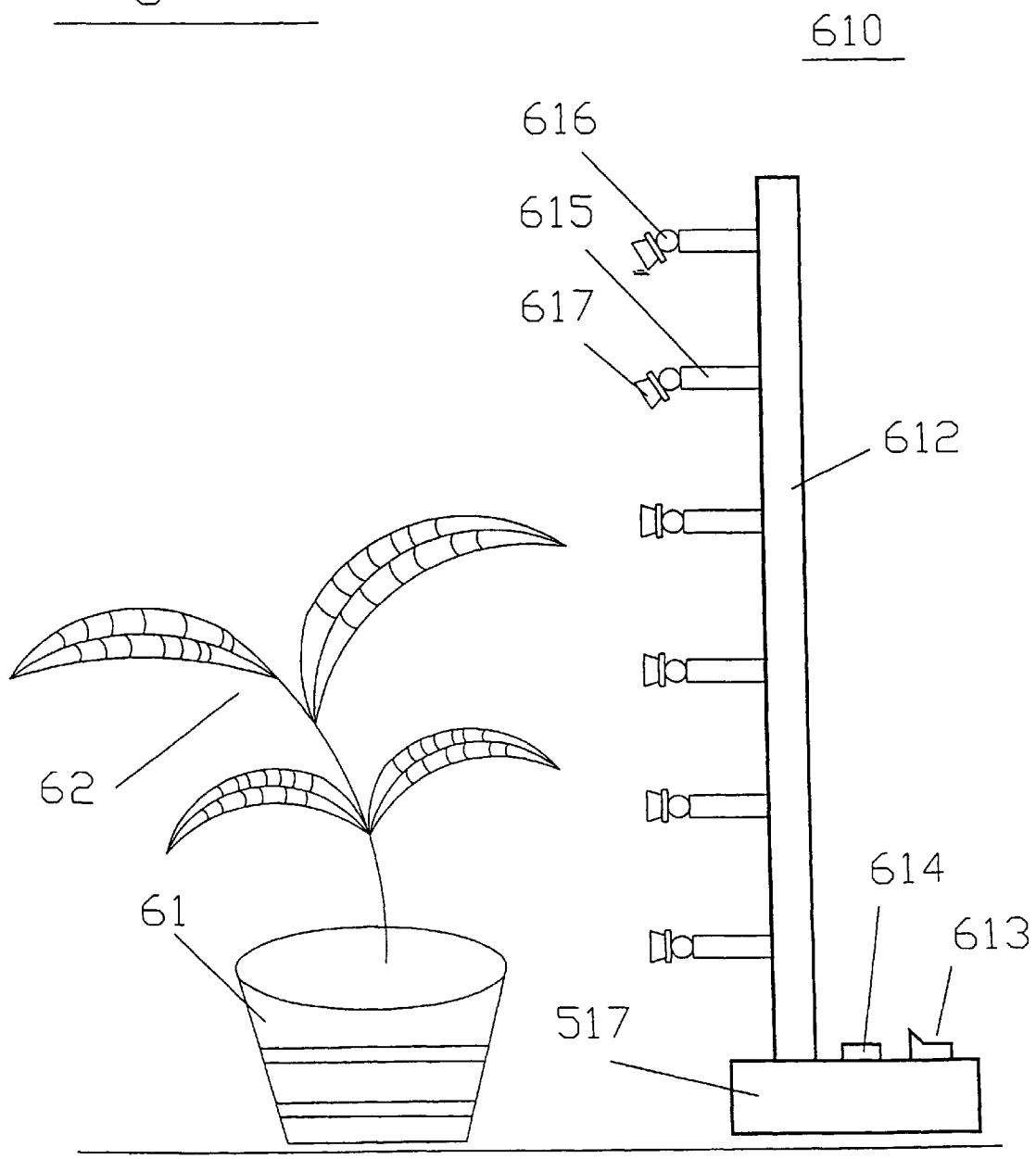

FIGS. 4A and 4B two embodiments of an apparatus for stimulating a patient's central nervous system;

FIG. 5 an embodiment of an apparatus for therapy and prophylaxis of decubitus; and FIGS. 6A and 6B two embodiments of an apparatus for biostimulation of plants.

FIG. 1 schematically shows an oral hygiene apparatus in the form of a water pick 100. This water pick 100 has a handle 1, at one end of which a tube-shaped mouthpiece 2 is located, while at its other end, a preferably flexible supply line 20 is provided, which serves both to supply water and to supply electricity. The pump (not shown) of the water pick can be arranged both in a water container (not shown) or in the handle 1. The on/off switch of the water pick 100 can also be provided either on the water container or on the handle 1, where the latter solution makes easier handling of the oral hygiene apparatus according to the invention possible.

As is evident from FIG. 1, a water channel 31 runs through the tube-shaped mouthpiece 2, and passes the water, which has been put under pressure by the pump, to a nozzle 3, which is only shown schematically. By means of the water which is given off by the nozzle 3, possibly in pulsating form, the teeth on which the water impacts are cleaned and the gums are massaged. The working method of such a water pick is generally known, so that no further explanation appears necessary.

According to the invention, a low-level laser irradiation device 10 is arranged within the handle 1, which generates a laser beam that is passed, via a light guide 11, which runs essentially parallel to the water channel 31 within the tube-shaped mouthpiece 2, to a lens 12, via which it finally exits. As is particularly evident in the sectional view A—A, the lens 12 is arranged slightly above the nozzle 3, in such a way that the laser beam is essentially directed at the gums when the water pick is used. If necessary, it is possible to use a lens with a large scatter range, so that correspondingly large regions of the gums are covered by the laser beam. Furthermore, it is possible to let the laser beam exit via several lenses.

The low-level laser irradiation device 10 is activated via a switch (not shown).

Instead of the water pick shown in the exemplary embodiment, the oral hygiene device according to the invention can also be an electric toothbrush. The low-level laser irradiation device 10 and particularly its lens 12 are arranged in analogous manner in this case. However, the low-level laser irradiation device 10 can also be a separate or independent part, for example in the form of a laser pen, which is added to the oral hygiene system in question.

Although this is not shown, a mechanical or optoelectronic sensor can be provided for the low-level laser irradiation device 10, which detects whether or not the mouth-side end of the mouthpiece 2, i.e. the lens 12, is located in the mouth. If this sensor detects that this is not the case, in other words that the mouthpiece 2 is located outside of the mouth cavity, a control device (not shown) switches the low-level laser irradiation device off, so that no laser beam, which might otherwise cause damage, is generated.

The low-level laser irradiation device according to the invention preferably uses a diode laser. However, it is also possible to use other suitable laser generation devices. The wavelength of the laser light generated lies in the range between 630 and 830 nm, in other words in the range of reddish light. If the range of the wavelength is extended up to 450 nm, greenish light is also emitted.

If necessary, it is also possible to operate the low-level laser irradiation device 10 not only continuously, but also in pulsating or other manner, with alternating output, if the therapeutic efficacy can be increased in this way. Corresponding control electronics can easily be integrated in the handle 1.

FIG. 2 shows an embodiment of the apparatus 200 according to the invention for therapy and prophylaxis of rhinitis and acne.

As is evident from FIG. 2, the apparatus 200 according to the invention has a housing 211, which is made of metal or a suitable plastic material, for example. The housing 211 is made in the manner of a handle, approximately round, so that the apparatus 200 can be held and operated in one hand.

In the interior of the housing 211, a rechargeable battery 250 is provided as a power supply; it can be charged by means of a charging device 260, which is plugged in, and is only shown schematically. As an alternative, the battery can also be a conventional, non-rechargeable battery; furthermore, it is possible to connect the apparatus to the electrical system directly via a line (and, if necessary, an additional transformer).

In the interior of the housing 211, a low-level laser irradiation device is provided, which consists of control electronics 214 which are supplied by the battery 250, and a laser beam transmission element in the form of a laser diode 216. The laser light generated by the laser diode 216 is fed into an oblong light-guide device 220, which can be inserted into a patient's nostril, for example. At the end of the light-guide device 220, there is a scatter lens 221 to spread out the laser beam emitted by the laser diode 216. The output of the laser diode 216 is between 1 mW and 5 mW and therefore corresponds to Class IIIA. The laser diode 16 generates a laser beam with a possible wavelength in the range from 180 nm to 1000 nm.

To turn the apparatus on, an on/off switch 230 is provided, while the output of the laser beam transmission element 216 can be adjusted by means of a rotary regulator 231.

As is evident from FIG. 2, the apparatus 200 can be held in one hand, in such a way that the end of the light-guide device 220 can be introduced into the nose in the simplest possible manner. The interior of the nose can therefore be effectively impacted by the laser light. Thus uniform and sufficient therapeutic treatment of the diseased nasal mucosa can be achieved with only a few manipulations.

The apparatus 200 described above can also be used for treatment of acne, according to the invention. Furthermore, it is possible to use this apparatus for stimulation of testosterone in the scrotum. Because of the increase in testosterone production provoked thereby, an improvement in the erectile potency of the patient in question will be achieved.

In order to allow the patient the easiest and most comfortable handling of the testosterone stimulation apparatus according to the invention that is possible, it is furthermore possible to structure the apparatus as a flexible wearable net or as a cushion in which the low-level laser irradiation device is arranged and which impacts the scrotum via several uniformly distributed laser beam transmission elements. Such a cushion can be placed around the scrotum and then worn while sitting, for example while reading or watching television.

According to FIG. 3A, a first embodiment of the inner-ear-disorder treatment apparatus according to the invention has a low-level laser irradiation device 310, which is built into the inside of a glasses frame 320, in the vicinity of its earpiece 321. The low-level laser irradiation device 310 is supplied with power via a cable 310*a*, from a power source (not shown) in the form of a battery or the like. The laser beam emitted by the low-level laser irradiation device 310 is passed, via a light-guide device 311, to a lens 312, from which it exits and acts on the region lying under it. The light-guide device 311 ends, on the exit side, in an approximately tube-shaped end piece 311*a*, which consists of an elastically deformable material, so that the position of the lens 312 and therefore the region of effect of the inner-ear-disorder treatment apparatus according to the invention can be changed, i.e. adapted to the patient. Since this first embodiment is integrated into a pair of glasses, a combination apparatus is created in this way, and it is hardly noticeable on a person who wears glasses.

FIG. 3B shows another embodiment of the inner-ear-disorder treatment apparatus according to the invention, which differs from the first embodiment in that the attachment device 320 is an earpiece which is made, for example, as a part made specifically for the inner-ear-disorder treatment apparatus. The earpiece 320 can, however, be part of a hearing aid, a tinnitus masker, or a combination apparatus consisting of a hearing aid and a tinnitus masker. For the remainder, this second embodiment of the inner-ear-disorder treatment apparatus corresponds to the first embodiment described above, so that with regard to its technical details, reference can be made to the above description.

FIG. 3C shows another embodiment of the inner-ear-disorder treatment apparatus according to the invention. In this embodiment, the inner-ear-disorder treatment apparatus is attached to a strap 330 configured to fit the inner-ear-disorder treatment apparatus over the patient's head in a similar manner as does a set of headphones.

In accordance with another embodiment of the invention, not shown in detail in the figures, the low-level laser irradiation device 310 can be a separate unit, which is worn in the patient's pocket or on the patient's belt, for example. In this case, the light-guide device 311 is a flexible line which ends in a lens, which can be attached to the ear by means of the attachment device. This embodiment of the invention is of particular advantage if the laser irradiation device 310 and/or its battery is relatively heavy.

For the low-level laser irradiation device 310, an on/off switch (not shown in the figures) can be provided, which makes it possible for the patient to perform the treatment at any desired time. The laser irradiation device 310 can furthermore have a manual adjustment device, by means of which its output and/or the wavelength of the laser beam can be adjusted to a suitable value. The laser irradiation device 10 operates either in continuous or pulsating operation, where a control device can be provided, if necessary, by means of which the desired mode of operation and/or the impulse frequency can be adjusted. The output of the laser irradiation device 310 is preferably between 1 and 120 mW. The wavelength of the laser beam lies in the range from 180 nm to 1000 nm. Therefore it is possible to use commercially available laser diodes as the radiation source.

Studies have shown that good healing results can be achieved with the apparatus according to the invention, particularly if the laser beam acts on the mastoid or on the middle ear, via the auditory canal. These regions of the ear can be irradiated by means of a suitable adjustment of the light-guide device 311. In order to achieve an even better healing effect, the apparatus according to the invention can be modified in such a way, if necessary, that two light-guide devices, each with its own lens, are provided, where the one lens acts on the mastoid and the other acts on the middle ear. The number of light-guide devices and lenses can, of course, be increased further, if other regions of the ear are to be therapeutically impacted, depending on the type of inner-ear disease.

According to FIG. 4A, a first embodiment of the apparatus according to the invention for stimulation of the central nervous system consists essentially of a helmet 41, which consists, for example, of foam material or another suitable plastic material, like a bicycle helmet. The helmet 41 has a plurality of suitable bores, with a low-level laser irradiation device 410 inserted into each of them. This low-level laser irradiation device 410 can either be a laser diode 411*a*, which has its own power supply, such as a battery, or a laser diode 11*b*, which is connected with a central power supply (not shown) via a power supply line 411*d*.

Inside the helmet 41, several spacers (not shown) are provided, which ensure that the exit openings of the laser diodes 411*a* or 411*b*, which are directed inward, have a predetermined distance from the patient's scalp. This has the result that the region of the patient's scalp assigned to each laser diode 411*a* or 411*b* is uniformly irradiated with a defined energy.

FIG. 4B shows another embodiment of the helmet, which differs from the embodiment of FIG. 4B in that light-guide devices 411*c* are provided as laser beam transmission elements, and these are supplied from a single light source (not shown). As an alternative to this, a separate laser light source can be provided for each or for at least part of the light-guide devices 411*c*, so that the possibility exists of operating some or all of the light-guide devices 411*c* with a different frequency and/or output. The laser light sources can either be part of the helmet 41 or be arranged in an external device.

The variant of the helmet shown in FIG. 4B therefore has the advantage that the wavelength and/or the energy of the laser beams can be centrally controlled, which makes it possible to simplify the control electronics, if necessary. At the end of each light-guide device 411c which lies inside the helmet 41, there is preferably a lens (not shown), which makes an even more advantageous, i.e. uniform distribution of the emitted laser light possible.

As is evident from FIG. 5, the apparatus according to the invention consists essentially of a housing 511, the apparatus for therapy and prophylaxis of decubitus according to the invention consists, for example, of metal or a suitable plastic material. The housing 511 has a plurality of suitable bores, with a tube 515 inserted in each of them, which forms a pivoting holder together with a joint 516. On this pivoting holder, a laser beam transmission element 517 is attached in each instance, which consists of a laser diode, for example. All the laser beam transmission elements, i.e. diodes 517 from the low-level laser irradiation device 510. The laser beam transmission elements 517 furthermore have a scatter lens, which is only shown schematically, to spread out the laser beam which they emit.

The housing 511 is attached to the ceiling or a suitable stand by means of devices which are not shown in detail; the housing 511 furthermore houses all the electrical and electronic components for controlling the laser beam transmission elements 517. To turn the apparatus on, an on/off switch (not shown) is provided, while the output of the laser beam transmission elements 517 can be adjusted by means of a rotary regulator.

As is evident from FIG. 5, the laser beam transmission elements 517 are directed at a patient (not shown) by means of the pivoting holders 515, 516; the patient is on a cot or bed 51. Because of the plurality of laser beam transmission elements 517 and because of the broad scattering of the laser beams produced by the scatter lenses, uniform and sufficient therapeutic treatment of the diseased, i.e. sore skin of the patient can be achieved with only a few manipulations.

Instead of separate laser beam transmission elements in the form of laser diodes 517, light-guide devices (not shown) can also be provided, which are supplied from a single light source (not shown), for example. The use of light guides furthermore has the advantage that the wavelength and/or energy of the laser beams can be centrally controlled, which makes it possible to simplify the control electronics, if necessary. The laser beam transmission elements 517 generate a laser beam with a wavelength in the range of 180 nm to 1000 nm, where the output preferably lies between 1 mW and 120 mW.

The housing 511 further comprises a manually operated timer (not shown), which deactivates the laser beam transmission elements 517 after a preselected time span has elapsed. The therapist can therefore leave the patient alone after setting or adjusting the apparatus, until the preselected time span has elapsed. Treatment periods of up to 30 minutes have proven to be advantageous in practice.

The laser beam transmission elements 517, i.e. their joints 516, can have a motor drive (not shown), which changes the emission angle of the laser beam transmission elements 517, so that the emitted laser beam essentially scans a corresponding region of the skin surface. This makes it possible to act on this region of the patient's skin with the laser beams in a cyclic sequence. Therefore the therapeutic effect can be made more uniform, if necessary. Furthermore, this makes it possible to use laser beam transmission elements 517 with a higher output, since the skin regions in question are only impacted for a short time, because of the motorized adjustment.

According to FIG. 6A, an embodiment of the apparatus for biostimulation of plants essentially consists of a stand 612, which consists, for example, of a tube made of metal or a suitable plastic. The stand 612 has a plurality of suitable bores, with a horizontally arranged rod 615 inserted in each of them, which forms a pivoting holder together with the joint 616. On this pivoting holder, a laser beam transmission element 617 is attached in each instance, which consists of a laser diode, for example. All the laser beam transmission elements, i.e. diodes 617, form the low-level laser irradiation device 10 according to the invention. The laser beam transmission elements 617 furthermore have a scatter lens, only indicated schematically, to spread out the laser beam they emit.

The stand 612 is attached in a housing 611, which simultaneously serves as a pedestal and houses all the electrical and electronic components for controlling the laser beam transmission elements 617. To turn the apparatus on, an on/off switch 613 is provided, while the output of the laser beam transmission elements 617 can be adjusted by means of a rotary regulator 614.

As is evident from FIG. 6A, the laser beam transmission elements 617 are directed at a plant 62, located in a pot 61, by means of the pivoting holder 615, 616. Because of the plurality of laser beam transmission elements 617 and because of the scattering of the laser beams produced by the scatter lenses, uniform and sufficient biostimulation of the plant 2 [sic] can be achieved with only a few manipulations.

FIG. 6B shows another embodiment of the apparatus according to the invention, which differs from the apparatus of FIG. 6A in that the laser beam transmission elements 617 and their pivoting holders 615, 616 are attached on a housing 611', which is intended to be mounted on a ceiling. For the remainder, this apparatus functions in the same manner as the apparatus of FIG. 6A.

Instead of separate laser beam transmission elements in the form of laser diodes, light-guide devices (not shown) can also be provided, which are supplied by a single light source (not shown), for example. This embodiment is well suited for larger spaces such as greenhouses and the like, if necessary. The use of light guides furthermore has the advantage that the wavelength and/or energy of the laser beams can be centrally controlled, which makes it possible to simplify the control electronics, if necessary.

The laser beam transmission elements 617 generate a laser beam with a wavelength in the range of *180* nm to 1000 nm, where the output preferably lies between 1 mW and 500 mW.

The housing 611 or 611' furthermore comprises a manually operated or automatic control device (not shown), which activates one or more of the laser beam transmission elements 617 with a suitable wavelength and/or changes its output, as a function of the growth phase of the plant 61. This makes an optimum adaptation to the growth of the plant 61 possible. Adjustment of the wavelength or the output can also be controlled by a timer, if the growth behavior of the plant 61 is known.

What is claimed is:

1. An inner-ear-disorder treatment apparatus for therapy of a chronic complex inner-ear disorder of a patient, comprising:

a low-level laser irradiation device; and an attachment device configured to releasably attach said low-level laser irradiation device to an ear of a patient in such a way that a laser beam acts on at least one predetermined region of the ear.

2. The inner-ear-disorder treatment apparatus according to claim 1, wherein the low-level laser irradiation device acts on at least one of a mastoid and a middle ear of said ear, via an auditory canal.

3. The inner-ear-disorder treatment apparatus according to claim 1, wherein the low-level laser irradiation device is housed in the attachment device and acts on the predetermined region of the ear via a light-guide device and a lens located at an end of said light-guide device.

4. The inner-ear-disorder treatment apparatus according to claim 1, wherein:

the low-level laser irradiation device is a separate unit, the laser beam passes, via a flexible light-guide device, through a lens located at an end of said flexible light-guide device, and at least one of the lens and the end of the light-guide device is configured to be attached to the ear by the attachment device.

5. The inner-ear-disorder treatment apparatus according to claim 1, wherein the attachment device is one of a glasses frame, a hearing aid, a tinnitus masker, and a combination apparatus comprising a tinnitus masker and a hearing aid.

6. The inner-ear-disorder treatment apparatus according to claim 1, wherein the attachment device is one of an earpiece configured to be attached to the ear, a part configured to be inserted into the ear, and a metal strap configured to be placed on the head.

\* \* \* \* \*